United States Patent [19]

Pankhania et al.

[11] Patent Number: 5,415,871
[45] Date of Patent: May 16, 1995

[54] THERAPEUTIC AGENTS

[75] Inventors: Mahendra G. Pankhania; Colin D. Melia; John F. Lampard, all of Nottingham, England

[73] Assignee: The Boots Company PLC, Nottingham, England

[21] Appl. No.: 687,090

[22] Filed: Apr. 19, 1991

Related U.S. Application Data

[63] Continuation of Ser. No. 320,694, Mar. 8, 1989, abandoned, which is a continuation of Ser. No. 2,158, Jan. 12, 1987, abandoned.

[30] Foreign Application Priority Data

Jan. 18, 1986 [GB] United Kingdom ............... 8601204

[51] Int. Cl.⁶ ............................................. A61K 9/26
[52] U.S. Cl. ..................................... 424/468; 424/469; 424/481; 424/482; 424/489
[58] Field of Search ............... 424/468, 482, 489, 469, 424/481

[56] References Cited

U.S. PATENT DOCUMENTS

| | | | |
|---|---|---|---|
| 3,065,143 | 11/1962 | Christenson et al. | 424/468 |
| 4,163,777 | 8/1979 | Mitra | 424/466 |
| 4,248,858 | 2/1981 | Guley et al. | 424/493 |
| 4,309,405 | 1/1982 | Guley et al. | 424/493 |
| 4,610,870 | 9/1986 | Jain et al. | 424/465 |
| 4,666,705 | 5/1987 | DeCrosta et al. | 424/482 |
| 4,717,713 | 1/1988 | Zatz et al. | 514/2 |
| 4,762,702 | 8/1988 | Gergey et al. | 424/489 |
| 4,994,276 | 2/1991 | Baichwal et al. | 424/440 |

FOREIGN PATENT DOCUMENTS

| | | |
|---|---|---|
| 103995 | 3/1984 | European Pat. Off. . |
| 181564 | 5/1986 | European Pat. Off. . |
| 182772 | 5/1986 | European Pat. Off. . |
| 190826 | 8/1986 | European Pat. Off. . |
| 200902 | 11/1986 | European Pat. Off. . |
| 2138492 | 1/1973 | France . |
| 901111 | 3/1985 | France . |
| 2126086 | 3/1948 | United Kingdom . |
| 1318169 | 5/1973 | United Kingdom . |
| 2067072 | 7/1981 | United Kingdom . |
| 2162528 | 2/1986 | United Kingdom . |
| 2165451 | 4/1986 | United Kingdom . |
| 8602834 | 5/1986 | WIPO . |
| 8705212 | 9/1987 | WIPO . |

OTHER PUBLICATIONS

Trade Literature: Xanthan gum/keltrol.
Kirk–Othmer Encyclopedia of Chemical Technology 3rd Ed., vol. 12, pp. 62–63, vol. 15, p. 447, p. 450.

Primary Examiner—Thurman K. Page
Assistant Examiner—Neil Levy
Attorney, Agent, or Firm—Nikaido, Marmelstein, Murray & Oram

[57] ABSTRACT

A sustained release pharmaceutical formulation comprising xanthan gum, a pharmaceutically active ingredient for example, ibuprofen or flurbiprofen, and other optional excipients.

65 Claims, No Drawings

THERAPEUTIC AGENTS

This application is a continuation of application Ser. No. 320,694, filed Mar. 8, 1989, now abandoned, which is a continuation of Ser. No. 002,158, filed Jan. 12, 1987, now abandoned.

This invention relates to controlled release formulations of therapeutic agents and in particular to sustained release formulations.

Sustained release formulations containing a pharmacologically active ingredient are employed where it is desired to administer a drug to a patient over a prolonged period without requiring the patient to take repeated doses of the drug at short intervals.

Substances which hydrate in an aqueous medium to form a gel are known to be used in combination with a pharmacologically active ingredient to provide a sustained release formulation in a solid dosage form. In such a solid dosage form, particles of the active ingredient are mixed with the hydratable substance. When the solid dosage form comes into contact with an aqueous medium, as is found in the gastro-intestinal tract for example, the hydratable substance swells to form a gel. Commonly the drug is released into the body by a combination of erosion and diffusion mechanisms depending on the nature of the gel formed.

Hydrophilic gums are known hydratable substances which provide controlled release formulations (see for example UK 131869 and U.S. Pat. No. 3,065,143). However, in order to provide sustained release sufficient to enable once or twice daily administration, the above references disclose that gums, such as galactomannans, sodium alginate, gum karaya, pectin, sodium polypectate and agar, must, in general, comprise a large proportion of the solid dosage form. It should be appreciated that not all gums having hydrophilic properties will be suitable per se to provide sustained release formulations.

Xanthan gum is one of many excipients suggested for use as a gelling or thickening agent in food and pharmaceutical preparations (see Kirk-Othmer Encyclopedia of Chemical Technology, 3rd Edition, vol. 15, p. 450). U.S. Pat. No. 4,163,777 relates to an antacid delivery form which dissolves over a period of up to one hour in the mouth. The formulation requires that the acid neutralization product is presented in a matrix including a sugar or a sugar alcohol; it also includes small proportions of a water insoluble lipid material and a gel-forming swelling agent which are used to produce a lozenge which is adapted to respond to the conditions found in the mouth to release the antacid product slowly. The gel forming, swelling agents used are said to be those pharmaceutically acceptable high molecular weight substances which swell and form a gel upon contact with water, including various gums, polysaccharides, cellulose derivatives and the like. Included among the examples of suitable swelling agents is xanthan gum. Xanthan gum is also known to have a synergistic swelling action in combination with locust bean gum (see for example Kirk-Othmer, 3rd Edition, vol. 15, p. 450). This combination is disclosed in UK 2165451 which relates to a tablet adapted to dissolve in the mouth over a period of up to two hours. These tablets require the presence of a very large proportion of monosaccharide or disaccharide (i.e. of the order of 70% or more), but only a very small amount of the xanthan/locust bean gum combination in order to function effectively to satisfy the particular requirements of a buccal tablet.

U.S. Pat. No. 4,248,858 relates to a 3 component sustained release composition for oral administration. It consists of a compressed core, a seal coating surrounding the core and a sugar coating containing a further dose of active ingredient surrounding the seal-coated core. The core formulations, in addition to the drug for which sustained release is desired, comprise about 30 to about 72% by weight of the core of a water soluble polymer and a water insoluble polymer mixture. It is proposed that xanthan gum is one of the pharmaceutically acceptable synthetic polymers and natural gums which may be employed as the water soluble polymer and that the water insoluble polymer may be ethylcellulose or a mixture of ethylcellulose with other synthetic polymers.

Unexpectedly, we have now found that xanthan gum itself has advantageous sustained release properties and in particular we have found that, where the sustained release carrier comprises a major proportion of xanthan gum, lower levels of sustained release carrier than heretofore suggested may be incorporated into a sustained release composition to provide a formulation with valuable sustained release properties. In such formulations the active ingredient is released slowly into the body over a prolonged period, and in particular allows once or twice daily administration of a drug to a patient.

Accordingly, the present invention provides a solid sustained release pharmaceutical formulation comprising a compressed mixture of a pharmacologically active ingredient and 7.5 to 28% by weight of the formulation of a sustained release carrier comprising a major proportion of xanthan gum.

Xanthan gum is a high molecular weight natural carbohydrate produced in a pure culture fermentation process by the xanthomonas campestris microorganism. In the fermentation process, xanthomonas campestris is cultured in a well-aerated medium containing glucose, a suitable nitrogen source, dipotassium hydrogen phosphate and trace elements. To provide seed for the final fermentation, the microorganism is grown in several stages with associated identification tests prior to introduction into the final fermentation medium. At the conclusion of the fermentation process, xanthan gum is recovered by precipitation in isopropyl alcohol and is then dried and milled.

Xanthan gum is less prone to natural variation, unlike naturally occuring gums, such as may occur with alginates and locust bean gum for example. It is of unvarying chemical structure and has uniform chemical and physical properties.

When the formulation comprising a sustained release carrier comprising a major proportion of xanthan gum, and the pharmacologically active ingredient comes into contact with an aqueous medium, as is found in the gastro-intestinal fluids, the xanthan gum in the portion of the formulation exposed to the aqueous medium hydrates and swells to form a gel. Xanthan gum has a good swelling action on contact with an aqueous medium and overcomes the problems encountered by gums which either do not hydrate rapidly enough or hydrate too rapidly. Gums which do not readily hydrate are generally unable to hold the tablet together as, on exposure to an aqueous medium, the tablet tends to break up before the gel fully hydrates. Gums which hydrate too rapidly generally also break up quickly as the gel formed is usually very weak and is unable to hold the tablet together. The thickness of the gel surrounding the central core of composition is intermediate between that of the thin layer when a hard gel is formed, as formed by hydroxypropylmethyl-cellulose gels for example, and the thick layer when a soft gel is formed. In addition the nature of the gel formed is such that unlike hard gels it may be readily deformed, unlike soft gels it is not disrupted by such deformation and in-vivo it may be expected to pass obstructions and not be impeded in the gastro-intestinal tract.

There is a graded reduction in the state of hydration of the xanthan gum in a formulation according to the invention, such that at the centre of the dose form a mixture of non-hydrated sustained release carrier comprising a major proportion of xanthan gum, pharmacologically active ingredient and other optional pharmaceutically acceptable excipients exists which will become fully hydrated with time. Unlike many controlled release solid dosage forms where the release rate decreases as the tablet is worn away, the nature and thickness of the gel formed in a formulation according to the invention enables a controlled and steady release of the drug into the body to occur. It is believed that erosion plays a part in the release of active ingredient from the solid composition, however, the gel formed is of sufficient thickness and abrasion resistance to allow diffusion to be the principle form by which the active ingredient is released into the body whether from the intact doseform or from smaller portions of drug containing gel that are eroded from it. This mechanism of release is advantageous over the more commonly known predominantly erosion mechanisms as it leads to a more controlled rate of release of the active ingredient into the body. In addition, by maintaining a layer of sufficiently constant proportions, through which diffusion may occur, a steady release of the medicament is achieved over a prolonged period of time. Such a formulation provides sufficient sustained release characteristics to enable a dose to be administered to a patient only once or twice daily. In addition, the gelling of xanthan gum is temperature independent; it is also pH independent and allows the active ingredient to diffuse out of the formulation at a steady rate as the medicament passes through the digestive system, irrespective of the pH. Thus the formulation is adapted to provide sustained release both in the acidic media of the stomach and also in the intestines. It will be realized that the actual rate of release will depend on the pH solubility of the pharmacologically active ingredient. In addition, formulations according to the invention have valuable storage properties. They also have advantageous processing properties and are particularly suitable for formulation into solid dosage forms.

It has been found the use of xanthan gum in the sustained release carrier generally allows a slower release of active ingredient into the body as compared to the use of naturally occurring hydrophilic gums. As a result, this provides the advantage that the proportion of sustained release carrier in the formulation may be reduced compared to most other sustained release formulations, thus enabling the sustained release formulation to be provided in a relatively small solid dosage form, if desired. As the proportion of sustained release carrier in the formulation is increased, the release of the active ingredient from the formulation is slowed. The amount of sustained release carrier employed in a formulation according to the invention is from 7.5 to 28% by weight of the formulation. Advantageously the sustained release carrier comprising a major proportion of xanthan gum comprises 10–25%, particularly 15–20%, by weight of the formulation.

The sustained release carrier is present to allow the release of the pharmacologically active ingredient from the formulation over a period of time greater than that expected from a conventional immediate release tablet. If desired, a proportion of the xanthan gum may be replaced in the sustained release carrier by one or more additional polymers having sustained release properties. We prefer to use not more than 50% by weight of the sustained release carrier of such other sustained release polymers; thus the sustained release carrier comprises a major proportion of xanthan gum. Examples of polymers having sustained release properties are water swellable polymers e.g. cellulose ethers, locust bean gum, guar gum, carboxyvinyl polymer, agar, acacia gum, sodium alginate or alginic acid, or film-forming polymers e.g. ethyl cellulose, hydroxypropyl methylcellulose phthalate or acrylic resin. Advantageous formulations according to the invention include a sustained release carrier comprising at least 75% by weight xanthan gum. Especially preferred formulations are those in which the sustained release carrier comprises at least 90% by weight xanthan gum.

The pharmacologically active ingredient may be any active ingredient suitable for use in sustained release formulations, especially aspirin and non-steroidal anti-inflammatory agents, in particular arylalkanoic acid, including their salts, esters, anhydrides, and other derivatives. These compounds are also antipyretics and analgesics. Other representative types of orally active medicaments which may be incorporated in the sustained-release formulations according to the invention include antihypertensives and other cardiovascular agents, anti-asthmatic agents, sedatives, stimulants, antibiotics, antispasmodics, nutritional agents, hematinics, anthelmintics, expectorants, hormones of various types including adrenocorticosteroids, androgenic steroids, estrogenic steroids, progestational steroids, and anabolic steroids, nonsteroidal counterparts of the foregoing, psychic energizers and antiviral agents of all of which types numerous specific embodiments are well known and will be both readily apparent and readily available to one skilled in the art. If desired, more than one pharmacologically active ingredient may be employed.

In a preferred formulation according to the invention the pharmacologically active ingredient comprises nonsteroidal anti-inflammatory agents, in particular arylalkanoic acids. Particularly suitable active ingredients for a formulation according to the invention are ibuprofen and flurbiprofen and their pharmaceutically acceptable salts. Especially advantageous sustained release properties are obtained when ibuprofen is combined with sustained release carrier comprising a major proportion of xanthan gum in a formulation according to the invention.

In particular, when formulations comprise ibuprofen and a sustained release carrier according to the present invention, the formulations are therapeutically effective and exhibit valuable bioavailability characteristics. Furthermore, the sustained release effect observed when ibuprofen is the pharmacologically active ingredient may occur for as long as 24 hours, or even longer. Such a formulation provides a "once a day" formulation, thus allowing the patient to take only one dose, comprising one or more unit dosage forms, a day in order to achieve a therapeutically effective level of active ingredient.

In a formulation according to the invention the pharmacologically active ingredient is mixed with the sustained release carrier and the mixture is compressed to produce a solid formulation. Preferably the ingredients are mixed to form a uniform dispersion and, for example, particles of the pharmacologically active ingredient may be in intimate admixture with particles of the sustained release carrier. Conveniently the sustained release carrier and pharmacologically active ingredient are dispersed substantially throughout the whole formulation.

Pharmaceutically acceptable excipients may also be incorporated into the sustained release formulation. Such pharmaceutically acceptable excipients may be added to modify the rate of drug dissolution and/or facilitate the manufacture of suitable dosage forms of the formulation.

For example, release-modifying pharmaceutically acceptable excipients that may be added in appropriate quantities for their particular ability to modify dissolution rates include, for example: stearic acid, metallic stearates, stearyl alcohol, hydrogenated cotton seed oil, polyethyleneglycol grades 4000 and 6000, surfactants such as sodium lauryl sulphate, polysorbates; lactose, sucrose, sodium chloride and tablet disintegrants for example corn starch, sodium starch glycollate, croscarmellose sodium and alginic acid. The quantity of such release-modifying excipient employed depends on the release characteristics required and the nature of the excipient. For a sustained release formulation according to the invention, the level of excipients used is suitably up to 25%, preferably up to 10% and advantageously up to 5% by weight of the total composition. Preferably the level of excipients is from 0.5–8% by weight, especially from 1–5% by weight.

The pharmaceutically acceptable excipients recognised by those skilled in the art, ie. formulation excipients, which may be necessary for the formation of suitable dosage forms include, but are not limited to, binders for example polyvinylpyrrolidone, gelatin, pregelled starches, microcrystalline cellulose; diluents for example lactose, sodium chloride, dextrins, calcium phosphate, calcium sulphate; lubricants for example stearic acid, magnesium stearate, calcium stearate, Precirol (trade mark) and flow aids for example talc or colloidal silicon dioxide. If necessary, such formulation excipients may be used in large quantities, particularly where the composition comprises a small amount of pharmacologically active ingredient. Preferably up to 50%, suitably up to 30% and especially up to 15% by weight of the composition of these above-mentioned excipients are employed.

The ratio of sustained release carrier comprising a major proportion of xanthan gum to pharmacologically active ingredient is preferably in the range 1:20 to 100:1.

For dosage forms containing a relatively high dose, in particular greater than 100 mg, of pharmacologically active ingredient, for example, ibuprofen, then the ratio of the sustained release carrier of the present invention to pharmacologically active ingredient may be in the range 1:20 to 1:1, suitably 1:15 to 1:1 parts by weight. More preferred ratios fall within 1:10 to 1:1, and advantageously 1:5 to 1:2 parts by weight of the sustained release carrier to pharmacologically active ingredient.

For dosage forms containing a relatively low dose of pharmacologically active ingredient, i.e. less than 100 mg and particularly less than 50 mg, the above ratios may be reversed in order to provide a solid dosage form of a suitable size for administration to a patient, i.e. preferably within the range of ratios 20:1 to 1:1, suitably 15:1 to 1:1, especially 10:1 to 1:1, and advantageously 5:1 to 2:1 parts by weight of sustained release carrier comprising a major proportion of xanthan gum to pharmacologically active ingredient. For very low dose pharmacologically active ingredients, i.e. particularly less than 10 mg, the ratio of sustained release carrier to pharmacologically active ingredient may be in the range 100:1 to 1:1, preferably 50:1 to 1:1 parts by weight.

Preferred formulations according to the invention are obtained when the compositions comprise 75–90% by weight ibuprofen and 10–25% by weight of a sustained release carrier comprising a major proportion of xanthan gum. Especially advantageous formulations comprise 85–90% by weight ibuprofen and 15–20% by weight of a sustained release carrier comprising a major proportion of xanthan gum.

Advantageously formulations according to the invention comprise 20–50% by weight flurbiprofen, 10–25% by weight of a sustained release carrier comprising a major proportion of xanthan gum, and 25–70% by weight pharmaceutically acceptable excipients, particularly 30–40% by weight flurbiprofen and 10–20% by weight of a sustained release carrier comprising a major proportion of xanthan gum together with 40–60% by weight of pharmaceutically acceptable excipients.

The sustained release medicament is provided in solid form, conveniently in a unit dosage form. It may be formed into any desired solid dosage presentation, for example gelatin capsules, tablets, lozenges, suppositories, pessaries or implants. It is preferred to provide the sustained release medicament in a solid unit dosage form for oral administration, especially in tablet form. Preferably, it is intended to release the pharmacologically active ingredient slowly after ingestion within the body as the formulation progresses along the gastro-intestinal tract. In this regard, the gastro-intestinal tract is considered to be the abdominal portion of the alimentary canal, i.e. the lower end of the oesophagus, the stomach and the intestines.

The solid dosage form of the sustained release medicament may optionally be provided with a coating of any conventional coating material, e.g. a film coating material.

A sustained release formulation according to the invention may be formed into a solid dosage presentation according to conventional processes. The pharmacologically active ingredient and sustained release carrier comprising a major proportion of xanthan gum together with other optional pharmaceutically acceptable excipients are mixed and then compressed to produce a solid formulation. In one such method the pharmacologically active ingredient is mixed with a minor proportion of the sustained release carrier of the present invention to form a dry mixture of powders. The mixture is then granulated using a binder material in a solvent such as an alcoholic solvent e.g. isopropyl alcohol or a mixture of a miscible organic solvent and an aqueous solvent. The wet granular mass is then dried. The other ingredients, including the remainder of the sustained release carrier of the present invention are dry mixed with the granules and compressed into tablets. Alternatively, if the nature of the active ingredient permits, all the ingredients may be dry mixed. For example, a metoclopramide sustained release tablet may be produced by dry mixing together the pharmacologically active ingredient, sustained release carrier of the present invention and suitable pharmaceutically acceptable tabletting excipients to form a homogeneous blend, which is then compressed to give a tablet of the correct weight.

The solid formulations according to the invention should be compressed to a sufficient hardness to prevent the premature ingress of the aqueous medium into the core. In a preferred process, wherein a formulation according to the invention is processed into tablet form, advantageously the hardness of the tablets is of the order of 8–20 kp as determined by a Schleuniger hardness tester.

Subject to the nature of the active ingredient, a formulation according to the invention is suitable for human or veterinary use.

The dosages of a formulation according to the invention correspond to the normal dosages of the particular active ingredient known to the man skilled in the art. The precise amount of drug administered to a patient will depend on a number of factors including the age of the patient, the severity of the condition and the past medical history, among other factors, and always lies within the sound discretion of the administering physician. For guidelines as to a suitable dosage, reference may be made to MIMS and to the Physicians Desk Reference.

As stated above, in a preferred pharmaceutical formulation according to the invention, the pharmacologically active ingredient is ibuprofen. Each dosage form suitably contains from 50 to 1200 mg of ibuprofen, preferably from 200 to 800 mg in one or more unit dosage forms. The daily dosage as employed for an adult human treatment is generally in the range from 100 to 3200 mg. Flurbiprofen is another pharmacologically active ingredient which may be used with advantage with a sustained release carrier comprising a major proportion of xanthan gum. Suitably the dosage of flurbiprofen is from 10–500 mg per day. Suitably the unit dose compositions of the present invention contain 10–250 mg, especially 25–100 mg of the active ingredient. The daily dosage of the drug is generally in the range 10–500 mg/day, more usually 30–300 mg/day.

A particular advantage of the sustained release formulations of this invention is that high levels of ibuprofen and other suitable drugs can be employed. Thus the present preferred compositions suitably comprise at least 50% by weight of ibuprofen, preferably at least 60–95%, especially from 75–90%.

In particular the provisions of a high dose composition having sustained release properties enables a unit dosage formulation of ibuprofen to be produced which is suitable for once- or twice-a-day administration, preferably once-a-day.

The invention is illustrated by the following non-limitative Examples.

In the Examples xanthan gum is supplied under the trade name Keltrol by Merck & Co. Inc., Kelco Division; colloidal silicon dioxide is supplied under the trade name Aerosil 200; polyvinylpyrrolidone is supplied under the trade name Plasdone K29-32; carrageenan gum is supplied under the trade name Genuvisco; sodium alginate is supplied under the trade name Manugel; microcystalline cellulose is supplied under the trade name Avicel PH101.

In each of Examples 1 to 18 T50 is the time taken for 50% of the active ingredient to be released from the tablet; T90 is the time taken for 90% of the active ingredient to be released from the tablet., These values were determined graphically. Graphs were plotted of the mean percent release of pharmacologically active ingredient vs time. A best fit line was drawn through these points. The T50 and T90 values were read off from this line.

EXAMPLE 1

Sustained release tablets comprising 800 mg ibuprofen were prepared from the following ingredients:

| Ingredient | mg/tablet |
|---|---|
| Ibuprofen | 800.0 |
| xanthan gum (Keltrol) | 196.9 |
| colloidal silicon dioxide (Aerosil 200) | 3.1 |
| polyvinylpyrrolidone (Plasdone K29-32) | 25.9 |
| Stearic acid | 10.4 |

Ibuprofen and 3% of the xanthan gum were deaggregated through a 6 mesh screen into a blender and the dry powders mixed for three minutes at high speed. A solution of polyvinylpyrrolidone prepared in isopropyl alcohol was added to the mixing powder over a 30 second period. Further mixing and addition of isopropyl alcohol was carried out to produce suitable granules.

The wet granular mass was discharged through a 4 mesh screen into the drying bowl of a fluid bed dryer. The granules were dried until the moisture level reached below ]% w/w. The dry granules were forced through a 16 mesh screen, weighed and blended with the remainder of the xanthan gum, together with colloidal silicon dioxide and stearic acid for 30 minutes. The blend was compressed on a tablet machine using pillow shaped tooling to produce tablets containing 800 mg of ibuprofen.

The hardness of tablets was determined on a Schleuniger hardness tester.

The release rate was determined using the US Pharmacopoeia, 1985, vol XXI apparatus 2. A single tablet was placed into the dissolution flask containing 900 ml of a buffered solution of desired pH, preheated to 37° C.±0.5° C. The buffer solution was rotated using paddle stirrers maintained at 100 rpm.

At one hour intervals, a small sample of approximately 2 ml supernatant liquid was withdrawn through a 1.2 μ membrane filter. The solution removed from the flask was analysed for the concentration of medicament released from the tablet. The procedure was continued until at least 90% of the tablet medicament had been released.

In order to correspond with the conditions the tablet is likely to meet in vivo as it passes along the gastrointestinal tract the following schedule of buffer solution was used. The pH was adjusted with 2M aqueous sodium hydroxide solution.

| Hours | pH |
|---|---|
| 0 | 2.5 |
| 1 | 4.5 |
| 2 | 4.5 |
| 3 | 6.8 |
| 4–24 | 6.8 |

The release characteristics of the 800 mg ibuprofen sustained release tablet of this Example are shown in Table 1.

TABLE 1

| Release Rate (hr) | Cumulative % of active ingredient released |
| --- | --- |
| 1 | 0.2 |
| 2 | 1.1 |
| 3 | 2.5 |
| 4 | 11.4 |
| 5 | 17.7 |
| 6 | 23.3 |
| 7 | 29.2 |
| 8 | 36.5 |
| 9 | 44.6 |
| 10 | 53.1 |
| 11 | 62.0 |
| 12 | 69.3 |
| 13 | 72.5 |
| 14 | 75.5 |
| 15 | 82.0 |
| 16 | 85.2 |
| 17 | 87.6 |
| 18 | 91.5 |
| HARDNESS 12-15 kp | |
| T50 9.5 hr | |
| T90 18 hr | |

A bioavailability study was conducted in 18 volunteers of the 800 mg sustained-release formulation of this Example compared to two standard Brufen 400 mg tablets. Brufen (Registered Trade Mark) is the proprietary name for ibuprofen and formulations thereof manufactured by The Boots Company PLC. The bioavailability is measured by the area under the plasma concentration vs time curves and is found to be satisfactory. After compensating for the effects of non-linear protein binding (Lockwood et al (1983) Clin. Pharm. Ther. 34(1)92) the area under the curve of the sustained-release formulation was 85% of that obtained following the immediate release reference formulation.

Three hours post-dose the plasma level achieved with the sustained-release formulation was 15 $\mu g.ml^{-1}$ Levels then slowly declined to approximately 10 $\mu g.ml^{-1}$ at six hours after which ibuprofen concentration again increases to give a second maximum of approximately 15 $\mu g.ml^{-1}$. The plasma levels of the formulation according to this Example at 12 and 24 hours post-dose were 15 and 3 $\mu g.ml^{-1}$ respectively compared to levels of 1 $\mu g.ml^{-1}$ and zero at 12 and 24 hours following the standard immediate release formulation of the Brufen (Registered Trade Mark) tablets.

There was no evidence of dose dumping in the sustained release formulation.

EXAMPLE 2

Sustained release tablets comprising 600 mg ibuprofen were prepared from the following ingredients:

| Ingredient | mg/tablet |
| --- | --- |
| Ibuprofen | 600.0 |
| Xanthan gum (Keltrol) | 61.8 |
| Hydroxypropylcellulose | 76.0 |
| Carrageenan gum (Genuvisco) | 20.5 |
| Lactose USP | 19.0 |
| Polyvinylpyrrolidone (Plasdone K29-32) | 15.0 |
| Stearic Acid | 8.2 |

The ibuprofen, hydroxypropyl-cellulose, polyvinylpyrrolidone and lactose USP were formed into granules by the deaggregation, dry mixing, granulation and drying processes as described in Example 1.

The dry granules were blended with the xanthan gum, carrageenan gum and stearic acid for 30 minutes and compressed on a tablet press using pillow shaped tooling to produce tablets containing 600 mg of ibuprofen. The hardness and the release rate of the 600 mg ibuprofen tablets of this Example were determined as described in Example 1. Table 2 shows the release characteristics of the 600 mg ibuprofen sustained release tablets.

TABLE 2

| Release Rate (hr) | Cumulative % of active ingredient released |
| --- | --- |
| 1 | 0.5 |
| 2 | 2.7 |
| 3 | 5.2 |
| 4 | 26.6 |
| 5 | 42.0 |
| 6 | 47.9 |
| 7 | 53.2 |
| 8 | 58.1 |
| 9 | 63.1 |
| 10 | 68.1 |
| 11 | 72.8 |
| 12 | 76.8 |
| 13 | 79.8 |
| 14 | 81.3 |
| 15 | 83.8 |
| 16 | 86.5 |
| 17 | 90.0 |
| HARDNESS 14-18 kp | |
| T50 6.5 hr | |
| T90 17.0 hr | |

EXAMPLE 3

Sustained release tablets comprising 800 mg ibuprofen were prepared from the following ingredients:

| Ingredient | mg/tablet |
| --- | --- |
| Ibuprofen | 800.0 |
| Xanthan gum (Keltrol) | 222.2 |
| Sodium alginate (Manugel) | 55.6 |
| Polyvinylpyrrolidone (Plasdone K29-32) | 22.2 |
| Stearic Acid | 11.1 |

The ibuprofen, sodium alginate and polyvinylpyrrolidone were formed into granules by the deaggregation, dry mixing, granulation and drying processes described in Example 1.

The dry granules were blended with the xanthan gum and stearic acid for 30 minutes and compressed on a tablet press using pillow shaped tooling to produce tablets containing 800 mg of ibuprofen.

The hardness and the release rate of the 800 mg ibuprofen tablets of this Example were determined as described in Example 1 to give the results shown in Table 3.

TABLE 3

| Release Rate (hr) | Cumulative % of active ingredient released |
| --- | --- |
| 1 | 0.1 |
| 2 | 0.6 |
| 3 | 2.0 |
| 4 | 13.0 |
| 5 | 25.6 |
| 6 | 38.5 |
| 7 | 51.7 |
| 8 | 60.4 |
| 9 | 66.4 |
| 10 | 71.7 |
| 11 | 77.3 |
| 12 | 81.9 |
| 13 | 83.9 |
| 14 | 85.8 |

TABLE 3-continued

| Release Rate (hr) | Cumulative % of active ingredient released |
| --- | --- |
| 15 | 92.1 |
| HARDNESS 10-13 kp | |
| T50 7 hr | |
| T90 14.7 hr | |

EXAMPLE 4

Sustained release tablets comprising 200 mg flurbiprofen were prepared from the following ingredients:

| Ingredient | mg/tablet |
| --- | --- |
| Flurbiprofen | 200.0 |
| Lactose USP | 242.4 |
| Xanthan gum (Keltrol) | 112.0 |
| Magnesium Stearate | 5.6 |

The flurbiprofen, lactose and xanthan gum were formed into granules by the deaggregation, dry mixing, granulation, and drying processes substantially as described in Example 1, but by using purified water as the granulating solvent.

The dry granules were blended with magnesium stearate and compressed on a tablet press to produce tablets containing 200 mg of flurbiprofen.

The hardness and release rate of the 200 mg flurbiprofen tablets of this Example were determined as described in Example 1 to give the following results shown in Table 4.

TABLE 4

| Release Rate (hr) | Cumulative % of active ingredient released |
| --- | --- |
| 1 | 0.3 |
| 2 | 0.3 |
| 3 | 1.22 |
| 4 | 6.3 |
| 5 | 12.87 |
| 6 | 15.06 |
| 7 | 20.44 |
| 24 | 98.3 |
| HARDNESS 9-11 kp | |
| T50 14 hr | |
| T90 23 hr | |

EXAMPLE 5

Sustained release tablets comprising 200 mg flurbiprofen were prepared from the following ingredients:

| Ingredient | mg/tablet |
| --- | --- |
| Flurbiprofen | 200.0 |
| Lactose USP | 298.4 |
| Xanthan gum (Keltrol) | 56.0 |
| Magnesium Stearate | 5.6 |

The flurbiprofen, lactose and xanthan gum were formed into granules by the deaggregation, dry mixing, granulation and drying processes substantially as described in Example 1 but by using purified water as the granulating solvent.

The dry granules were blended with magnesium stearate and compressed on a tablet press to produce tablets containing 200 mg of flurbiprofen.

The hardness and the release rate of the 200 mg flurbiprofen tablets of this Example were determined as described in Example 1 to give the results shown in Table 5.

TABLE 5

| Release Rate (hr) | Cumulative % of active ingredient released |
| --- | --- |
| 1 | 0.3 |
| 2 | 2.0 |
| 3 | 2.1 |
| 4 | 19.0 |
| 5 | 37.0 |
| 6 | 62.5 |
| 7 | 68.5 |
| 8 | 71.5 |
| 9 | 74.0 |
| 10 | 75.0 |
| 12 | 81.5 |
| 14 | 89.5 |
| 16 | 95.0 |
| HARDNESS 9-11 kp | |
| T50 5-6 hr | |
| T90 14 hr | |

Examples 6–18 comprise sustained release formulations produced in a similar manner to that described in Example 1. Table 6 indicates the ingredients and their proportion in the formulation. The amount of each ingredient is shown as a percentage of the weight of the tablet; the percentage of the sustained release carrier is also shown as a percentage weight of the total tablet. Table 6 also shows the hardness and T50 and T90 values for each formulation.

TABLE 6

| Example Ibuprofen content (mg) per tablet | 6 800 mg | 7 800 mg | 8 600 mg | 9 600 mg | 10 800 mg | 11 800 mg | 12 800 mg | 13 800 mg | 14 800 mg | 15 800 mg |
| --- | --- | --- | --- | --- | --- | --- | --- | --- | --- | --- |
| Xanthan gum (Keltrol) | 10.0% | 15.0% | 5.0% | 2.5% | 7.5% | 10.0% | 13.0% | 13.0% | 20.0% | 23.0% |
| Carrageenan gum (Genuvisco) | — | — | 2.5% | 2.5% | — | — | — | — | — | — |
| Sodium alginate (Manugel) | — | — | — | — | 7.5% | 5.0% | 5.0% | 5.0% | 5.0% | 3.0% |
| Hydroxypropyl cellulose | — | — | — | — | — | — | — | — | — | — |
| Polyvinyl pyrrolidone (Plasdone K29-32) | 2.0% | 2.0% | 2.0% | 2.0% | 1.0% | 2.0% | 2.0% | 2.0% | 2.0% | 2.0% |
| Stearic acid | 1.0% | 1.0% | 1.0% | 3.0% | 1.0% | 1.0% | 1.0% | 1.0% | 1.0% | 1.0% |
| microcrystalline cellulose (Avicel PH101) | — | — | — | — | — | — | 2.0% | — | — | — |
| Lactose USP | — | — | 5.0% | 6.0% | — | — | — | — | — | — |

TABLE 6-continued

| Example Ibuprofen content (mg) per tablet | 6 800 mg | 7 800 mg | 8 600 mg | 9 600 mg | 10 800 mg | 11 800 mg | 12 800 mg | 13 800 mg | 14 800 mg | 15 800 mg |
|---|---|---|---|---|---|---|---|---|---|---|
| SUSTAINED RELEASE CARRIER | 10% | 15% | 7.5% | 5% | 15% | 15% | 18% | 18% | 25% | 26% |
| HARDNESS (kp) | 12.2 | 13.1 | — | 15.2 | 10.5 | 12.9 | 11.6 | 13.9 | 13.3 | 14.9 |
| T50 (hr) | 6.4 | 7.8 | 3.5 | 4.5 | 5.7 | 7.0 | 5.0 | 5.9 | 7.4 | 9.0 |
| T90 (hr) | 19.0 | 19.0 | 7.5 | 10.0 | 8.5 | 9.8 | 8.6 | 9.8 | 11.7 | 22.5 |

EXAMPLE 16

Sustained release tablets containing 40 mg metoclopramide were prepared in a similar manner to that described in Example 1 from the following ingredients:

| Ingredient | % w/w |
|---|---|
| Metoclopramide Hydrochloride | 12.3 |
| Xanthan gum (Keltrol) | 28.0 |
| Microcrystalline cellulose (Avicel PH101) | 43.9 |
| Polyvinylpyrrolidone (Plasdone K29-32) | 2.5 |
| Lactose BP | 12.3 |
| Stearic Acid | 1.0 |

The release rate of a proprietary immediate release tablet [Maxolon (Registered Trade Mark) supplied by Beecham Group PLC, Brentford, Middlesex, UK] containing 10 mg metoclopramide was compared to the release rate obtained with the above-described sustained release formulation. The release rate was determined using the US Pharmacopoeia, 1985, vol. XXI apparatus 2. A single tablet was placed into the dissolution flask containing 900 ml of a buffered solution at pH 7.2, preheated to 37° C.±0.5° C. The buffer solution was rotated using paddle stirrers maintained at 100 rpm. At one hour intervals, a small sample of supernatant liquid was withdrawn through a 1.2 μ membrane filter. The solution removed from the flask was analysed for the concentration of medicament released from the tablet. The procedure was continued until at least 90% of the tablet medicament had been released. The results are shown in Table 7 below.

TABLE 7

| | % Drug Released from the System | |
|---|---|---|
| Time (min) | Proprietary Immediate Release Tablet | Sustained Release Table According to the Invention |
| 5 | 100 | — |
| 10 | | — |
| 20 | | — |
| 30 | | 14 |
| 60 | | 23 |
| 120 | | 37 |
| 180 | | 51 |
| 240 | | 63 |
| 300 | | 67 |
| 360 | | 73 |
| 420 | | 79 |
| 480 | | 85 |
| 540 | | 92 |
| 600 | | 98 |
| 720 | | |
| 900 | | |
| 1200 | | |
| T50 | 2 min | 2.9 hr |
| T90 | 4 min | 8.7 hr |

EXAMPLE 17

Sustained release tablets containing 150 mg indomethacin were prepared in the same way as described in Example 1 from the following ingredients:

| Ingredient | % w/w |
|---|---|
| Indomethacin | 46.1 |
| Xanthan gum (Keltrol) | 23.0 |
| Microcrystalline cellulose (Avicel PH101) | 15.0 |
| Polyvinylpyrrolidone (Plasdone K29-32) | 2.5 |
| Lactose | 12.3 |
| Stearic Acid | 1.0 |
| Isopropyl alcohol q.s. | |

The release rate of the above-described sustained release tablet containing 150 mg indomethacin was compared with
a) a proprietary immediate release tablet [Indocid (Registered Trade Mark); Thomas Marson Pharmaceutical (Merck Sharpe & Dohme Ltd., Herts., UK)] containing 50 mg indomethacin; and
b) a proprietary sustained release tablet [Indocid R (Registered Trade Mark); Thomas Marson Pharmaceutical (Merck Sharpe & Dohme Ltd., Herts., UK)] containing 75 mg indomethacin.

The release rates were determined in the described in Example 16.

The results are shown in Table 8 below.

TABLE 8

| | % Drug Released from the System | | |
|---|---|---|---|
| Time (min) | (a) Proprietary Immediate Release Tablet | (b) Proprietary Sustained Release Tablet | Sustained Release Tablet According to the Invention |
| 5 | 73 | — | — |
| 10 | 95 | — | — |
| 15 | 100 | — | — |
| 20 | 100 | — | — |
| 30 | | 66.6 | — |
| 60 | | 90.3 | 4.0 |
| 120 | | 96.9 | 6.0 |
| 180 | | | 9.0 |
| 240 | | | 15.0 |
| 300 | | | 24.0 |
| 360 | | | 39.0 |
| 420 | | | 59.0 |
| 480 | | | 86.0 |
| 540 | | | 93.0 |
| 600 | | | 96.0 |
| 720 | | | 99.0 |
| 900 | | | 100.0 |
| 1200 | | | |
| T50 | 2.5 min | 18 min | 6.6 hr |
| T90 | 8.5 min | 60 min | 8.6 hr |

EXAMPLE 18

Sustained release tablets containing 300 mg theophylline were prepared in the same manner as described in Example 1 from the following ingredients:

| Ingredient | % w/w |
|---|---|
| Theophylline BP (anhydrous) | 46.1 |
| Xanthan gum (Keltrol) | 28.0 |
| Microcrystalline cellulose (Avicel PH101) | 10.0 |
| Lactose BP | 12.3 |
| Polyvinylpyrrolidone (Plasdone K29-32) | 2.5 |
| Stearic Acid | 1.0 |
| Isopropyl Alcohol | qs |

The release rate of the above-described sustained release tablet containing 300 mg theophylline was compared with a) a proprietary immediate release tablet [Tedral (Registered Trade Mark); Parke-Davis, Hants., IrK] containing 120 mg theophylline; and b) a proprietary sustained release tablet [Theo-Dur (Registered Trade Mark), Fisons Pharmaceuticals Ltd., Leics., IrK] containing 300 mg theophylline.

The release rates were determined in the same manner described in Example 16.

The results are shown in Table 9 below.

| | % Drug Released from the System | | |
|---|---|---|---|
| Time (min) | (a) Proprietary Immediate Release Tablet | (b) Proprietary Sustained Release Tablet | Sustained Release Tablet According to the Invention |
| 5 | 85.5 | | |
| 10 | 100 | | |
| 20 | | | |
| 30 | | | |
| 60 | | 18.7 | 6.2 |
| 120 | | 29.4 | 12.3 |
| 180 | | 40.8 | 17.5 |
| 240 | | 55.3 | 22.8 |
| 300 | | 77.0 | 27.9 |
| 360 | | 90.8 | 32.4 |
| 420 | | 95.2 | 36.2 |
| 480 | | 97.6 | 40.9 |
| 540 | | | 45.0 |
| 600 | | | 49.8 |
| 720 | | | 57.2 |
| 900 | | | 69.2 |
| 1200 | | | 91.0 |
| T50 | 2 min | 3.5 hr | 10 hr |
| T90 | 5 min | 6.0 hr | 20 hr |

We claim:

1. A method of treating inflammation, pain and/or fever in a patient in need of such treatment which comprises administering to the patient a therapeutically effective amount of a sustained release pharmaceutical formulation in tablet form, which formulation consists essentially of a compressed mixture of a therapeutically effective amount of ibuprofen or a pharmaceutically acceptable salt thereof in an amount of 75 to 90% by weight of the formulation in combination with a sustained release carrier in an amount of 10-25% by weight of the formulation, wherein xanthan gum is present in the sustained release carrier to an extent of at least 75% by weight of the sustained release carrier.

2. Method of claim 1 wherein the ratio of xanthan gum to ibuprofen or salt thereof is in the range of 1:10 to 1:1 parts by weight.

3. Method of claim 1 wherein xanthan gum is present in the sustained release carrier to an extent of at least 90% by weight of the sustained release carrier.

4. Method of claim 1 wherein the sustained release carrier consists essentially of xanthan gum.

5. Method of claim 4 wherein the tablet contains 50-1200 mg ibuprofen.

6. Method of claim 4 wherein the tablet contains 200-800 mg ibuprofen.

7. Method of claim 4 wherein the sustained release carrier is present in an amount of 15-20% by weight of the formulation.

8. Method of claim 4 wherein the ratio of xanthan gum to ibuprofen or salt thereof is in the range 1:5 to 1:2 parts by weight.

9. A method of administering ibuprofen or a pharmaceutically acceptable salt thereof in a sustained release dosage form to a patient in need thereof, said method comprising administering to the patient a solid unit dose which consists essentially of a compressed mixture of a therapeutically effective amount of ibuprofen or salt thereof and a sustained release carrier comprising xanthan gum present to an extent of at least 75% by weight of said carrier, wherein the sustained release carrier is present in an amount of 10-25% by weight of the mixture, the ratio of xanthan gum to ibuprofen or salt thereof being in the range 1:10 to 1:1 parts by weight.

10. Method of claim 9 wherein the ibuprofen or salt thereof is present in an amount of 75-90% by weight of the mixture.

11. Method of claim 9 wherein the sustained release dosage form contains 50-1200 mg ibuprofen or salt thereof.

12. Method of claim 9 wherein xanthan gum is present in the sustained release carrier to an extent of at least 90% by weight of said sustained release carrier.

13. Method of claim 9 wherein the sustained release carrier consists essentially of xanthan gum.

14. A solid sustained release pharmaceutical tablet consisting essentially of a compressed mixture of a therapeutically effective amount of ibuprofen or a pharmacologically acceptable salt thereof present in an amount of from 75 to 90% by weight of the tablet and a sustained release carrier present in an amount of from 10 to 25% by weight of the tablet, wherein xanthan gum is present in the sustained release carrier to an extent of at least 75% by weight of the sustained release carrier, and wherein the amount of said sustained release carrier is such as to result in a tablet, when in a gastrointestinal tract, releases ibuprofen or salt thereof over an extended period of time such that one or more tablets need to be introduced into the gastrointestinal tract only once or twice a day to maintain the release of an effective amount of ibuprofen or salt thereof.

15. Tablet of claim 14 containing 50-1200 mg ibuprofen or salt thereof.

16. Tablet of claim 14 containing 200-800 mg ibuprofen or salt thereof.

17. Tablet of claim 14 wherein the ratio of xanthan gum to ibuprofen or salt thereof is in range of 1:10 to 1:1 parts by weight.

18. Tablet of claim 14 wherein xanthan gum is present in the sustained release carrier to an extent of at least 90% by weight of the sustained release carrier.

19. Tablet of claim 14 wherein the sustained release carrier consists essentially of xanthan gum.

20. Tablet of claim 14 wherein the sustained release carrier is present in an amount of 15-20% by weight of the formulation.

21. Tablet of claim 14 wherein the sustained release rate of ibuprofen or salt thereof from the tablet, as determined by the in vitro U.S. Pharmacopoeia, 1985, Vol. XXI apparatus 2 test, is such that is requires at least about 14 hours to release 90% of the active ingredient in the tablet.

22. Tablet of claim 19 containing 50-1200 mg ibuprofen or salt thereof.

23. Tablet of claim 19 containing 200-800 mg ibuprofen or salt thereof.

24. Tablet of claim 19 wherein the ratio of xanthan gum to ibuprofen or salt thereof is in the range of 1:10 to 1:1 parts by weight.

25. Tablet of claim 19 wherein the sustained release carrier is present in an amount of 15-20% by weight of the formulation.

26. A process for the preparation of a solid sustained release pharmaceutical composition in tablet form which consists essentially of mixing a sustained release carrier, which sustained release carrier comprises at least 75% by weight of the carrier xanthan gum, with 50-1200 mg ibuprofen or salt thereof by first mixing said ibuprofen or salt thereof with a minor proportion of said sustained release carrier to form a dry powder mixture, granulating the powder mixture, drying the granulated powder mixture, adding the remainder of the sustained release carrier to the dry granulated mixture and compressing the mixture to form a solid tablet consisting essentially of a mixture of 10-25% sustained release carrier and 75-90% ibuprofen or salt thereof.

27. Formulation for preparing solid dosage forms having a regular and sustained release, characterized by consisting essentially of an effective amount of a pharmaceutically active substance and 7.5-28 weight percent of a sustained release carrier being a homogeneous mixture of substances imparting a retard effect, said sustained release carrier consisting essentially of 50-100 weight percent of xanthan gum, said pharmaceutically active substance being intimately admixed into said sustained release carrier.

28. Formulation of claim 27 for preparing solid dosage forms having a regular and sustained release, characterized by consisting essentially of said active substance and 10-25 weight percent of a sustained release carrier, imparting a retard effect, said sustained release carrier consisting essentially of 50-100 weight percent of xanthan gum and 0-50 weight percent of one or more natural or synthetic polymers.

29. Formulation according to claim 28, characterized in that the percentage by weight of sustained release carrier components is 50-100% of xanthan gum and 0-50% of one or more of said polymers.

30. Formulation according to claim 28, characterized in that the sustained release carrier comprises, in addition to xanthan gum, at least one cellulose ether.

31. Formulation according to claim 27 formulated into a sustained release pharmaceutical solid dosage form.

32. Formulation according to claim 28 wherein in addition to said active substance and constituents of the sustained release carrier, an inert excipient used for obtaining the desired dosage form, selected from and lubricants and diluents, are present.

33. Formulation according to claim 28 characterized in that the sustained release carrier has such a composition as to prolong the drug release up to 24 hours so as to allow one single administration per day.

34. A formulation of claim 31 wherein the dosage form is an oral dosage form.

35. A formulation of claim 34, wherein the oral dosage form is a tablet, capsule or lozenge.

36. A method of treating inflammation, pain and/or fever in a patient in need of such treatment which comprises administering to the patient a therapeutically effective amount of a sustained release pharmaceutical formulation in tablet form, which formulation consists essentially of a compressed mixture of a therapeutically effective amount of non-steroidal anti-inflammatory agent or a pharmaceutically acceptable salt thereof in combination with a sustained release carrier which is present in an amount of about 7.5 to about 28% by weight of the formulation, wherein xanthan gum is present in the sustained release carrier to an extent of a major proportion of the sustained release carrier.

37. Method of claim 36 wherein the ratio of xanthan gum to said agent or salt thereof is in the range of 1:10 to 10:1 parts by weight.

38. Method of claim 36 wherein xanthan gum is present in the sustained release carrier to an extent of at least 90% by weight of the sustained release carrier.

39. Method of claim 36 wherein the sustained release carrier consists essentially of xanthan gum.

40. Method of claim 39 wherein the tablet contains 50-1200 mg of said agent or salt thereof.

41. Method of claim 39 wherein the tablet contains 200-800 mg ibuprofen.

42. Method of claim 39 wherein the sustained release carrier is present in an amount of 15-20% by weight of the formulation.

43. Method of claim 39 wherein the ratio of xanthan gum to said agent or salt thereof is in the range 1:5 to 1:2 parts by weight.

44. A method of administering a pharmaceutically active agent or a pharmaceutically acceptable salt thereof in a sustained release dosage form to a patient in need thereof, said method comprising administering to the patient a solid unit dose which consists essentially of a compressed mixture of a therapeutically effective amount of said agent or salt thereof and a sustained release carrier consisting essentially of xanthan gum present in a major proportion by weight in said carrier, wherein the sustained release carrier is present in an amount of about 7.5 to about 28% by weight of the mixture, the ratio of xanthan gum to said agent or salt thereof being in the range 1:20 to 100:1 parts by weight.

45. Method of claim 44 wherein the agent or salt thereof is present in an amount of 75-90% by weight of the mixture.

46. Method of claim 44 wherein the sustained release dosage form contains 50-1200 mg agent or salt thereof.

47. Method of claim 44 wherein xanthan gum is present in the sustained release carrier to an extent of at least 90% by weight of said sustained release carrier.

48. Method of claim 44 wherein the sustained release carrier consists essentially of xanthan gum.

49. A solid sustained release pharmaceutical tablet consisting essentially of a compressed mixture of a therapeutically effective amount of a pharmacologically active ingredient and a sustained release carrier present in an amount of from about 7.5 to 28% by weight of the tablet, wherein xanthan gum is present in the sustained release carrier in a major proportion, and wherein the amount of said sustained release carrier is such as to result in a tablet, when in a gastrointestinal tract, which releases said ingredient thereof over an extended period of time such that one or more tablets need to be introduced into the gastrointestinal tract only once or twice a day to maintain the release of an effective amount of said ingredient.

50. Tablet of claim 49 containing 50–1200 mg of said agent or salt thereof.

51. Tablet of claim 49 containing 200–800 mg of said agent or salt thereof.

52. Tablet of claim 49 wherein the ratio of xanthan gum to said agent or salt thereof is in range of 1:10 to 1:1 parts by weight.

53. Tablet of claim 49 wherein xanthan gum is present in the sustained release carrier to an extent of at least 90% by weight of the sustained release carrier.

54. Tablet of claim 49 wherein the sustained release carrier consists essentially of xanthan gum.

55. Tablet of claim 49 wherein the sustained release carrier is present in an amount of 15–20% by weight of the formulation.

56. Tablet of claim 49 wherein the ingredient is ibuprofen and the sustained release rate of said or salt thereof from the tablet, as determined by the in vitro U.S. Pharmacopoeia, 1985, Vol. XXI apparatus 2 test, is such that it requires at least about 14 hours to release 90% of the active ingredient in the tablet.

57. Tablet of claim 54 containing 50–1200 mg of said active ingredient.

58. Tablet of claim 54 containing 200–800 mg of said active ingredient.

59. Tablet of claim 54 wherein the ratio of xanthan gum to said ingredient or salt thereof is in the range of 1:10 to 10:1 parts by weight.

60. Tablet of claim 54 wherein the sustained release carrier is present in an amount of 10–25% by weight of the formulation.

61. A process for the preparation of a solid sustained release pharmaceutical composition in tablet form which consists essentially of mixing a sustained release carrier, which sustained release carrier comprises at least a major proportion by weight of the carrier of xanthan gum, with a pharmacologically active ingredient thereof by first mixing said ingredient with a minor proportion of said sustained release carrier to form a dry powder mixture, granulating the powder mixture, drying the granulated powder mixture, adding the remainder of the sustained release carrier to the dry granulated-mixture and compressing the mixture to form a solid tablet consisting essentially of a mixture of about 7.5 to 28% by weight of sustained release carrier and an effective amount of said ingredient.

62. Method of claim 39, wherein the sustained release carrier is present in an amount of about 10 to about 25% by weight of the formulation.

63. Method of claim 48, wherein the sustained release carrier is present in an amount of about 10 to about 25% by weight of the formulation.

64. A tablet of claim 54 wherein the active ingredient is flurbiprofen or a pharmaceutically acceptable salt thereof.

65. A tablet of claim 64 comprising 10–25% by weight of a sustained release carrier comprising xanthan gum and 20–50% by weight flurbiprofen or a pharmaceutically acceptable salt thereof.

* * * * *